United States Patent
Gramckow et al.

(10) Patent No.: US 6,679,626 B2
(45) Date of Patent: Jan. 20, 2004

(54) METHOD FOR DETERMINING THE THERMAL MATERIALS PROPERTIES OF SHAPED METAL PARTS

(75) Inventors: Otto Gramckow, Uttenreuth (DE); Michael Jansen, Möhrendorf (DE); Martin Post, Geldern (DE); Klaus Weinzierl, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/377,338

(22) Filed: Feb. 28, 2003

(65) Prior Publication Data

US 2003/0136479 A1 Jul. 24, 2003

Related U.S. Application Data

(63) Continuation of application No. PCT/DE01/03127, filed on Aug. 16, 2001.

(30) Foreign Application Priority Data

Aug. 29, 2000 (DE) .......................... 100 42 386

(51) Int. Cl.[7] .......................... G01K 11/00; G06F 1/00; B22C 1/00
(52) U.S. Cl. .......................... 374/43; 703/2; 164/154.6; 164/154.7
(58) Field of Search .......................... 374/43, 45, 159, 374/44; 703/2; 164/151.4, 154.1, 154.6–154.7, 451, 449, 4.1, 154.5

(56) References Cited

U.S. PATENT DOCUMENTS

| | | | |
|---|---|---|---|
| 4,588,443 A | * 5/1986 | Bache | .......................... 106/97 |
| 4,913,878 A | * 4/1990 | Dawson et al. | .......................... 420/18 |
| 5,893,055 A | 4/1999 | Chen | .......................... 702/189 |
| 6,044,895 A | 4/2000 | Kuttner et al. | .......................... 164/155.4 |

FOREIGN PATENT DOCUMENTS

| | | | |
|---|---|---|---|
| DE | 43 38 608 A1 | 8/1995 | .......... G05B/17/02 |
| DE | 197 17 615 A1 | 10/1998 | .......... B22D/11/22 |
| DE | 198 50 253 A1 | 5/2000 | .......... G05B/13/04 |
| JP | 04080324 | 3/1992 | .......... C21D/9/52 |
| JP | 04232214 | 8/1992 | .......... C21D/11/00 |

OTHER PUBLICATIONS

Derwent Information Ltd. Fifferentialthermal analyzer–has narrow gap to pass gas from heat sensor zone to reaction zone and uses gas to prevent aggressive substance reaching sensors. Chirik et al. Jan. 1987.*

Derwent Information Ltd. Unit for thermal analysis of metals and alloys has two coaxial refractory containers, with electrically ignited mixture between, to heat and allow cooling curve to be plotted. Kazachkov et al. Oct. 1981.*

Thermal Analysis of Continuous Casting Process, Kiflie et al. ESME 5th Annual Conference of Manufacturing and Process Industry. Sep. 2000.*

* cited by examiner

*Primary Examiner*—Gail Verbitsky
(74) *Attorney, Agent, or Firm*—Baker Botts L.L.P.

(57) ABSTRACT

A method for determining the thermal material properties of metal shaped parts from a model is disclosed, which describes the thermal material properties of the metal shaped part. At least one thermodynamic parameter (p) is formed as a linear combination consisting of at least one base function (hi) and of at least one weighting factor (gi), whereby the base function (hi) describes the thermal material properties, and the weighting factor (gi) takes the influence of the alloying elements on at least one thermodynamic parameter (p) into account. The method makes it possible to conduct a sufficiently precise determination of the thermal material properties with a smaller time requirement.

9 Claims, 2 Drawing Sheets

METHOD FOR DETERMINING THE THERMAL MATERIALS PROPERTIES OF SHAPED METAL PARTS

CROSS REFERENCE TO RELATED APPLICATION

This application is a continuation of copending International Application No. PCT/DE01/03127 filed Aug. 16, 2001, which designates the United States.

BACKGROUND OF THE INVENTION

The invention relates to a method for determining the thermal materials properties of shaped metal parts.

In certain technological processes, such as for example the cooling of hot-roll steel strips, it is necessary or desirable for the thermal materials properties of the shaped metal parts to be determined as accurately as possible. During the cooling of hot-roll steel strips, the microstructural properties of the rolled steel strips are adjusted during passage through the cooling section of the hot-rolling mill train, the microstructural properties being adjusted primarily by means of the quantity of water supplied. To calculate the quantity of water required, a cooling section model based on Fourier's thermal conductivity equation is used. This model can be used to calculate the temperature distribution in the steel strip during the cooling operation.

One difficulty which arises in the modelling is the relatively strong dependent relationship between the thermal materials properties and the alloying elements which have been added. By way of example, the thermal conductivity at 500° C. drops by about 50% as a result of the addition of 1% of chromium.

On account of the relatively strong dependent relationship between the thermal materials properties and the alloying elements which have been added, these elements have to be determined relatively accurately. Hitherto, this has been achieved by means of measurements at the thermodynamic equilibrium. The specific approach for the chemical dependency may, for example, involve describing the thermal conductivity of the material, which is a function of the temperature, by means of an open polygon. The coordinates of the associated supporting points are in this case made dependent on the alloying elements which are contained in the material. These dependent relationships, which are determined directly on the plant in question, are summarized in table form. In the most simple case, the sum of the alloying elements is used. Free parameters are determined by means of a compensating calculation on the basis of measurement.

Obtaining sufficiently accurate values in the method described is a very time-consuming process.

SUMMARY OF THE INVENTION

It is an object of the invention to provide a method which makes it possible, within a short time, to make it possible to sufficiently accurately determine the thermal materials properties.

This object can be achieved by a method according to the invention, in which the thermal material properties of shaped metal parts are determined from a model which describes the thermal materials properties of the shaped metal part, in which
at least one thermodynamic parameter P is formed as a linear combination of at least one basic function hi and at least one weighting factor gi in accordance with the relationship $$p = \pm \sum_{i=1}^{n} g_i \cdot h_i + c, n \in N, c = \text{const.} \quad \text{or}$$

$$p = \pm \sum_{i=1}^{n} (g_i + c_i) \cdot h_i, n \in N, c_i = \text{const.} \quad \text{and}$$

the basic function hi describes the thermal materials properties, and
the weighting factor gi takes account of the influence of the alloying elements on at least one thermodynamic parameter P.

The methods described in the independent claims represent a combination of a physical model and data-assisted methods for preventing a material model, the thermal materials properties being formed, according to the invention, by at least one linear combination of at least one basic function hi and at least one weighting factor gi. Therefore, the methods according to the invention do not require a concrete approach for the dependent relationship of the alloying elements, which is difficult to describe. Furthermore, the alloying elements can be taken into account in highly differentiated form. As a result, given a sufficient number of measurement data, it is possible to obtain a very accurate material model.

The thermal materials properties, which are defined by the thermodynamic parameter p and can be described by at least one basic function, are, for example, the enthalpy, the heat capacity and the thermal conductivity.

In the context of the invention, the basic functions used may be, for example, as alternatives or in combination, rectangular blocks, sawteeth, B splines, preferably 4th order B splines, or Gaussian bells.

If the linear combination consists exclusively of rectangular blocks, a step function results for the thermodynamic parameter p.

Given a linear combination exclusively comprising sawteeth (first order B splines), an open polygon is obtained for the thermodynamic parameter p.

If exclusively 4th order B splines are used to form a linear combination, a cubic spline is obtained for the thermodynamic parameter p.

In an advantageous configuration of the method according to the invention, the weighting factors gi are determined in a neural network from the mass contents of the alloying elements which have been added and/or variables derived therefrom.

A predeterminable number of data sets, which each include measurements of surface temperatures and velocity and information about the quantities of water required for cooling for a specific hot-rolled steel strip, is used to train the neural network. The respective steel strips may—but do not have to—in this case have different concentrations of alloying elements.

The data sets include measurements for at least approximately pure iron. A model is determined from these parts of the data sets and is matched to reality. The thermodynamic parameters for pure iron are known, and consequently matching of the model to reality is carried out only for the heat transfer. Then, the entire data set, which also includes measurements for alloyed steels, is taken into consideration. A possible deviation from the model which has previously been matched to reality is determined from this data set. This deviation can only be explained by alloying contents which are present in the material, and not by the cooling operation (water quantity and water temperature). The calculations are matched to the measurements by changing the network weights wi. The change in the network weights Wi leads to a change in the weighting factors gi. The calculations are matched to the measurements until the calculations correspond sufficiently well to the measurements for all the shaped parts (e.g. steel strips).

As an alternative to determining weighting factors gi in a neural network, it is possible for weighting factors gi to be determined by a linear combination of the mass content of at least one alloying element and/or variables derived therefrom and a regression factor.

BRIEF DESCRIPTION OF THE DRAWINGS

Further advantageous configurations of the invention are explained in more detail below with reference to two exemplary embodiments which are illustrated in the drawing, in which, in outline form.

DETAILED DESCRIPTION OF THE PREFERRED EMBODIMENTS

In the method according to the invention, the thermal materials properties of shaped metal parts are determined from a model which describes the thermal materials properties of the shaped metal part, in which at least one thermodynamic parameter P is formed as a linear combination of at least one basic function hi and at least one weighting factor gi in accordance with the relationship $$p = \pm \sum_{i=1}^{n} g_i \cdot h_i + c, \, n \in N, \, c = const., \quad N = Natural\ Numbers.$$

or $$p = \pm \sum_{i=1}^{n} (g_i + c_i) \cdot h_i, \, n \in N, \, c_i = const.$$

and the basic function (hi) describes the thermal materials properties, and the weighting factor (gi) takes account of the influence of the alloying elements on at least one thermodynamic parameter (p).

Figure 1:
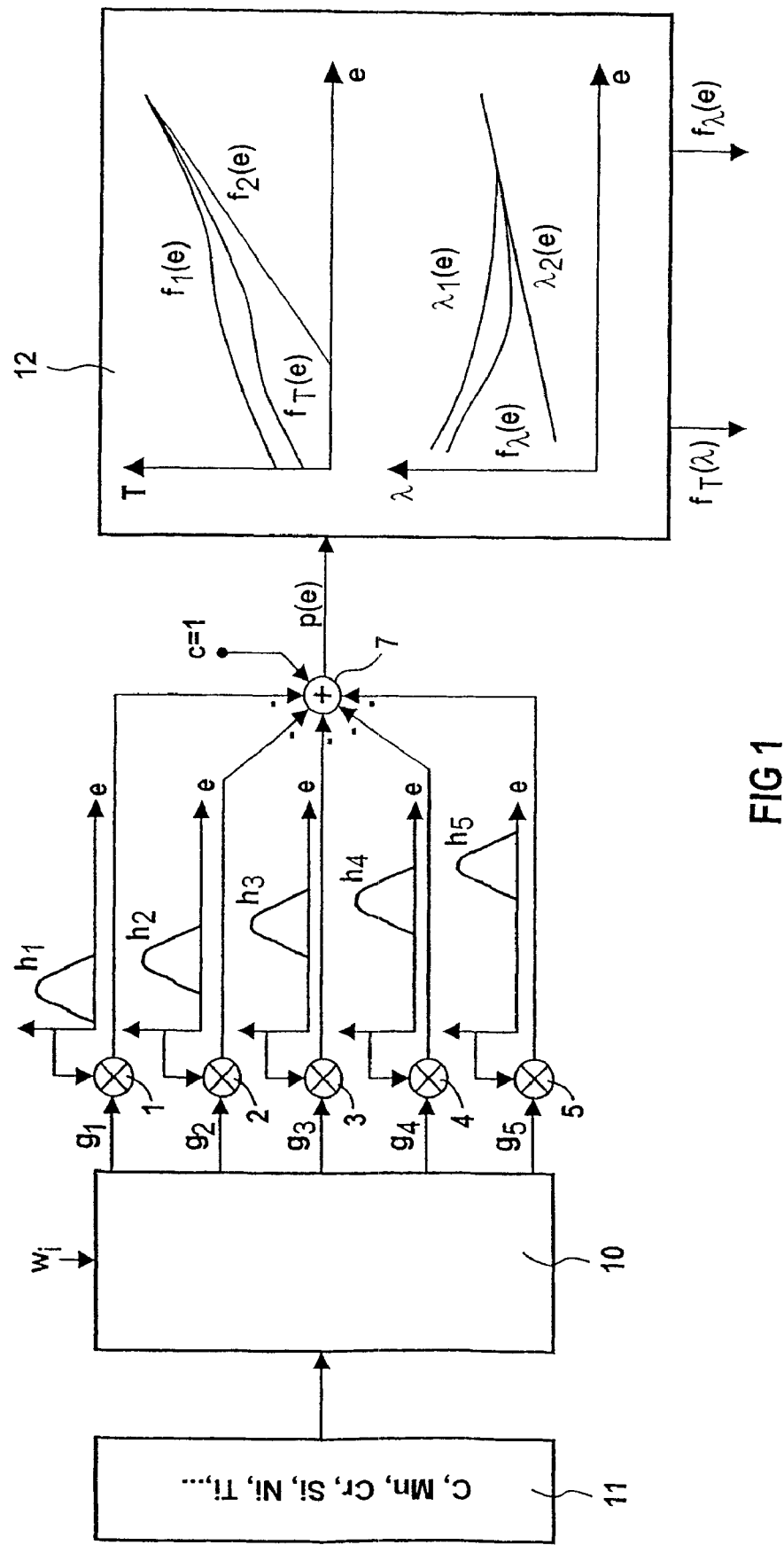
FIG. 1 shows a block diagram of a first embodiment of the method according to the invention.

In the exemplary embodiment shown in FIG. 1, the thermal materials properties of hot-rolled steel strips are determined. In the embodiment illustrated, all five basic functions h1 to h5 are 4th order B splines. Therefore, a spline consisting of third degree polynomials is obtained for the thermodynamic parameter p which describes the thermal materials properties of the shaped part.

In the exemplary embodiment shown in FIG. 1, the materials property described by the thermodynamic parameter p is the degree of conversion of austenite into ferrite as a function of the enthalpy e. However, in the context of the invention it is also possible, by way of example, to describe thermal materials properties by means of the heat capacity and/or the thermal conductivity.

In the configuration shown in FIG. 1, the weighting factors g1 to g5 are determined in a neural network 10 from the mass contents of the alloying elements (C, Mn, Cr, Si, Ni, Ti, . . . ) which have been added to the steel and the network weights Wi. The network weights wi are obtained by training the neural network 10 (also referred to as optimization) and/or fed to the neural network 10 by a data memory (not shown in FIG. 1).

The alloying elements which have been added to the steel are made available as data sets by a data memory 11. A predeterminable number of these data sets which, in addition to the alloying contents for a specific hot-rolled steel strip, also include the measurements of surface temperatures and details about the quantities of water required for cooling, is used to train the neural network 10. The respective steel strips may in this case also have different concentrations of alloying elements.

Each of the basic functions h1 to h5 available as fourth order B splines is multiplied by in each case one weighting factor g1 to g5 and by (−1) in a multiplier 1 to 5 and is fed to an adder 6. In the exemplary embodiment illustrated, the value c=1 for the alloy-independent constant c is also fed to the adder 6. Therefore, the value $$p(e) = -\sum_{i=1}^{5} g_i \cdot h_i + 1,$$

is available for p(e) at the output of the adder 6.

With p(e) as the degree of conversion of austenite into ferrite (or pearlite) as a function of the enthalpy e, the following functional relationship, which has been determined in functional block 12, between the enthalpy e and the temperature T results:

$$f_T(e) = p(e) f_1(e) + [1\ p(e)] f_2(e).$$

The following functional relationship, which is likewise determined in the functional block 12, is then obtained for the thermal conductivity λ and the enthalpy e:

$$f_{80}(e) = p(e) \cdot \lambda_1(e) + [1 - p(e)] \cdot \lambda_2(e).$$

If all the weighting factors gi=0, i.e. if no alloying elements have been admixed with the steel, p(e) is then approximately 1, i.e. pure ferrite or pearlite is present.

Therefore, for the functional relationship between the enthalpy e and the temperature T, the following relationship is obtained:

$$fT(e) = f1(e).$$

This then results in the following equation for the functional relationship between the thermal conductivity λ and the enthalpy e:

$$f\lambda(e) = \lambda(e).$$

By contrast, if p(e)≡0, i.e. for pure austenite, the following functional relationships are obtained:

$$fT(e) = f2(e).$$

$$f\lambda(e) = \lambda2(e).$$

However, if p(e) is defined as the original austenite content, and not (as in the exemplary embodiment shown in FIG. 1) as the degree of conversion of austenite into ferrite, $$p = \sum_{i=1}^{n} g_i \cdot h_i + c, \; n \in N,$$

where c=0 is to be selected for the equation.

In this case, if $p(e) \cong 0$, pure ferrite or pearlite is present, whereas if $p(e) \cong 1$ pure austenite is present.

In this case, the indices 1 and 2 need to be swapped over in the functional relationships for fT(e) and fλ(e).

Figure 2:
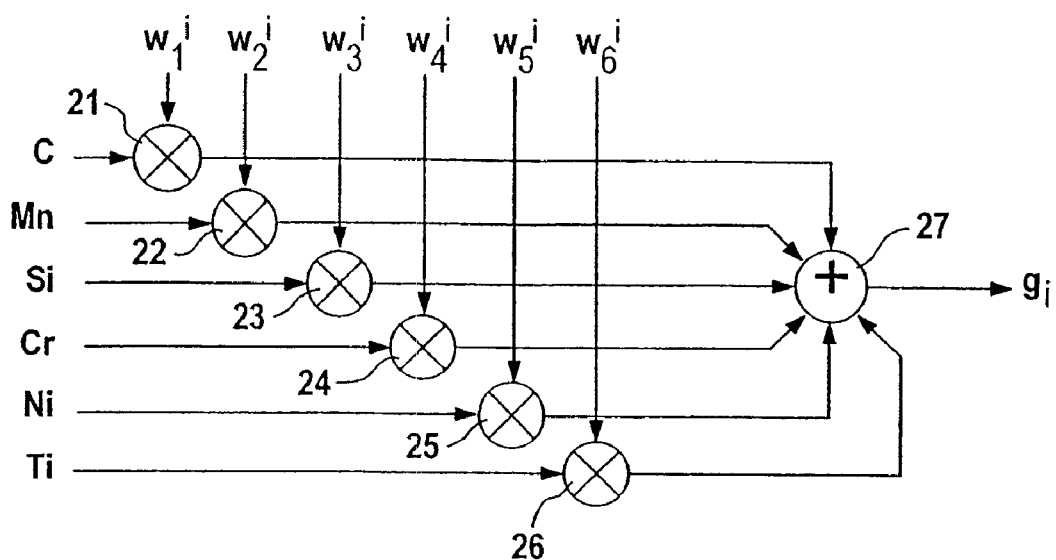
FIG. 2 shows a determination of the weighting factors which represent an alternative to the method shown in FIG. 1.

As an alternative to determining a weighting factor gi in a neural network 10, it is also possible for this weighting factor gi to be determined by a linear combination of the mass contents of the alloying element C, Mn, Cr, Si, Ni, Ti, in each case with a regression factor $w^i_1$ to $w^i_6$. According to FIG. 2, the six linear combinations are determined in each case one multiplier 21 to 26 and are fed to an adder 27, which uses them to determine a weighting factor gi.

This weighting factor gi is processed further in the functional block 12 in the manner which has been shown in FIG. 1.

Figure 3:
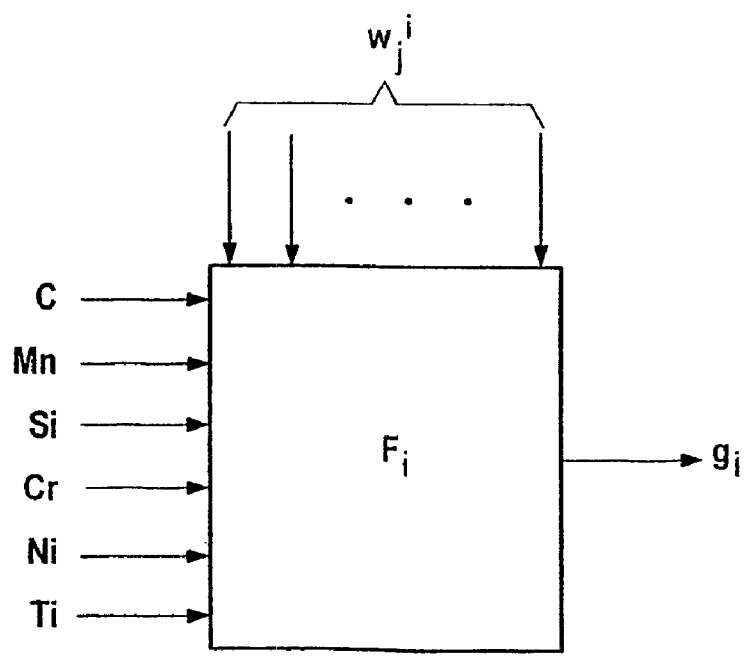
FIG. 3 shows a determination of the weighting factors which represents an alternative to the method shown in FIG. 1 and FIG. 2.

As an alternative to determining a weighting factor gi in a neural network 10 (FIG. 1) or a linear combination (FIG. 2), this weighting factor gi can also be formed from the mass contents of the alloying elements C, Mn, Cr, Si, Ni, Ti with at least one free parameter $w^i_j$ by means of a nonlinear function. In accordance with FIG. 3, the six alloying elements and the free parameters $w^i_j$ are fed to the nonlinear function Fi of a plurality of variables. The result of the nonlinear function Fi is the weighting factor gi.

Alternatively, it is also possible to add/or remove alloying elements. By way of example, it is also possible to use a combination comprising C, Mn, Cr, Si, V.

What is claimed is:

1. A method for determining the thermal materials properties of shaped metal parts from a model which describes the thermal materials properties of the shaped metal part, wherein at least one thermodynamic parameter is formed as a linear combination of at least one basic function hi and at least one weighting factor gi in accordance with the relationship $$p = \pm \sum_{i=1}^{n} g_i \cdot h_i + c, \; n \in N, \; c = const.$$

and the basic function hi describes the thermal materials properties, and the weighting factor gi takes account of the influence of the alloying elements on at least one thermodynamic parameter p.

2. The method as claimed in claim 1, wherein the thermal materials properties which are described by at least one basic function hi are at least one of the thermal materials properties selected from the group consisting of temperature, enthalpy, heat capacity, and thermal conductivity.

3. The method as claimed in claim 1, wherein a rectangular block is selected for at least one basic function hi.

4. The method as claimed in claim 1, wherein a sawtooth is selected for at least one basic function hi.

5. The method as claimed in claim 1, wherein a B spline, preferably a fourth order B spline, is selected for at least one basic function hi.

6. The method as claimed in claim 1, wherein a Gaussian function is selected for at least one basic function hi.

7. The method as claimed in claim 1, wherein at least one weighting factor gi is the output variable of a neural network, to which at least one alloying element and/or at least one variable derived therefrom and at least one network weight are fed as input variables.

8. The method as claimed in claim 1, wherein at least one weighting factor gi is determined from at least one linear combination of the mass content of at least one alloying element and/or variables derived therefrom and at least one regression factor.

9. The method as claimed in claim 1, wherein at least one weighting factor gi is formed from at least one linear combination of the mass content of at least one alloying element and/or at least one variable derived therefrom and at least one free parameter of a nonlinear function.

\* \* \* \* \*